United States Patent
Greenawalt et al.

(10) Patent No.: US 11,953,480 B2
(45) Date of Patent: Apr. 9, 2024

(54) AQUEOUS PERACETIC ACID DETECTION

(71) Applicant: HACH COMPANY, Loveland, CO (US)

(72) Inventors: Angella Nicholle Greenawalt, Loveland, CO (US); Darren Kent MacFarland, Windsor, CO (US)

(73) Assignee: HACH COMPANY, Loveland, CO (US)

( * ) Notice: Subject to any disclaimer, the term of this patent is extended or adjusted under 35 U.S.C. 154(b) by 727 days.

(21) Appl. No.: 17/058,610

(22) PCT Filed: Jun. 27, 2019

(86) PCT No.: PCT/US2019/039566
§ 371 (c)(1),
(2) Date: Nov. 24, 2020

(87) PCT Pub. No.: WO2020/006272
PCT Pub. Date: Jan. 2, 2020

(65) Prior Publication Data
US 2021/0208119 A1     Jul. 8, 2021

Related U.S. Application Data (60) Provisional application No. 62/692,187, filed on Jun. 29, 2018.

(51) Int. Cl.
| | |
|---|---|
| *G01N 21/78* | (2006.01) |
| *A01N 37/16* | (2006.01) |
| *A01N 59/00* | (2006.01) |
| *C02F 1/72* | (2023.01) |
| *G01N 21/63* | (2006.01) |
| *G01N 31/22* | (2006.01) |

(52) U.S. Cl.
CPC ........... *G01N 31/226* (2013.01); *A01N 37/16* (2013.01); *A01N 59/00* (2013.01); *C02F 1/722* (2013.01); *G01N 21/63* (2013.01); *C02F 2303/04* (2013.01)

(58) Field of Classification Search
None
See application file for complete search history.

(56) References Cited

U.S. PATENT DOCUMENTS

| | | | |
|---|---|---|---|
| 6,329,207 B1 | 12/2001 | Fricker et al. | |
| 7,651,860 B2 | 1/2010 | Howarth et al. | |
| 2013/0327718 A1* | 12/2013 | Adami | B63J 4/002 |
| | | | 210/96.1 |

FOREIGN PATENT DOCUMENTS

| | | |
|---|---|---|
| CN | 107037045 A | 8/2017 |
| WO | 2018017809 A1 | 1/2018 |

OTHER PUBLICATIONS

International Searching Authority Notification of Transmittal of the International Search Report and the Written Opinion of the International Searching Authority, or the Declaration, dated Dec. 17, 2019; pp. 16.

* cited by examiner

Primary Examiner — Paul S Hyun
(74) Attorney, Agent, or Firm — Ference & Associates LLC (57) ABSTRACT

An embodiment provides a method for measuring peracetic acid concentration in an aqueous solution, including: combining, in a reactive solution, 4-(methylthio)aniline and at least one reactive species to produce a chromophore, wherein the at least one reactive species comprises a chromotropic acid disodium salt; placing the chromophore in an aqueous solution, wherein the aqueous solution comprises peracetic acid, wherein peracetic acid within the aqueous solution reacts with the chromophore; and measuring a concentration of peracetic acid within the aqueous solution, wherein the measuring comprises quantifying a colorimetric change of the aqueous solution caused by the peracetic acid reacting with the chromophore. Other embodiments are described and claimed.

12 Claims, 7 Drawing Sheets

AQUEOUS PERACETIC ACID DETECTION

BACKGROUND

The disinfection of drinking water is an important task for water treatment facilities. Other uses such as agriculture, meat processing, food, beverage, and medical industries rely on disinfection as well. Disinfection may serve to clean drinking water of bacteria and organisms harmful to humans and animals. Disinfection may also be used to clean animal or other food products prior to packaging or serving. Some of these industries use chlorine or chlorine based products for disinfection. The use of chlorine may also be used to clean systems used in the water, agriculture, or medical fields.

Although chlorine and chlorine products are widely used for disinfection, there may be some drawbacks. Chlorine may be detectable in both the taste and smell of drinking water. Workers performing disinfection protocols may be exposed to higher levels of chlorine which may cause skin irritation or pulmonary irritation. Chlorine may be corrosive to tanks, pipes, or the like, through which the chlorine travels. This corrosion may lead to unintended consequences. For example, disinfection of pipes made of lead may be corroded by chlorine products which in turn releases more lead into the water which may be ingested by humans.

BRIEF SUMMARY

One embodiment provides a method for measuring peracetic acid concentration in an aqueous solution, comprising: combining, in a reactive solution, 4-(methylthio)aniline and at least one reactive species to produce a chromophore, wherein the at least one reactive species comprises a chromotropic acid disodium salt; placing the chromophore in an aqueous solution, wherein the aqueous solution comprises peracetic acid, wherein peracetic acid within the aqueous solution reacts with the chromophore; and measuring a concentration of peracetic acid within the aqueous solution, wherein the measuring comprises quantifying a colorimetric change of the aqueous solution caused by the peracetic acid reacting with the chromophore.

Another embodiment provides a method for measuring peracetic acid concentration in an aqueous solution, comprising: combining, in a reactive solution, 4-(methylthio) aniline and at least one reactive species to produce a chromophore, wherein the at least one reactive species comprises sodium 2-naphthol-6-sulfonate hydrate; placing the chromophore in an aqueous solution, wherein the aqueous solution comprises peracetic acid, wherein peracetic acid within the aqueous solution reacts with the chromophore; and measuring a concentration of peracetic acid, wherein the measuring comprises quantifying a colorimetric change of the aqueous solution caused by the peracetic acid reacting with the chromophore.

A further embodiment provides a method for measuring peracetic acid concentration in an aqueous solution, comprising: placing a chromophore in an aqueous solution, wherein the aqueous solution comprises peracetic acid, wherein peracetic acid within the aqueous solution reacts with the chromophore; measuring a concentration of peracetic acid, wherein the measuring comprises quantifying a colorimetric change of the aqueous solution caused by the peracetic acid reacting with the chromophore.

The foregoing is a summary and thus may contain simplifications, generalizations, and omissions of detail; consequently, those skilled in the art will appreciate that the summary is illustrative only and is not intended to be in any way limiting.

For a better understanding of the embodiments, together with other and further features and advantages thereof, reference is made to the following description, taken in conjunction with the accompanying drawings. The scope of the invention will be pointed out in the appended claims.

DETAILED DESCRIPTION

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

References throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well known structures, materials, or operations are not shown or described in detail to avoid obfuscation.

Chlorine is often used as a disinfectant. Chlorine may be used to treat municipal water, wastewater, medical equipment, food and beverage equipment, or the like. Chlorine may be effective in treating water and equipment by targeting organisms. These organisms may be killed through the oxidation of cellular material via the use of the chlorine. Chlorine exists in many different forms, for example, chlorine gas, hypochlorite solutions, other chlorine compounds in both liquid and solid forms, or the like. A decision of which disinfectant to use may be based on many factors. These factors may include the ability of a selected agent to destroy infectious agents in a given condition, safety, handling, storage, cost, and an agent's properties with respect to toxic residual, mutagenic, or carcinogenic properties of the agent.

The use of chlorine for disinfection has advantages and disadvantages. Some advantages of chlorine disinfection include a long history of use, lower cost as compared to other agents, disinfection to a wide spectrum of pathogens, and residual disinfection. However, chlorine does have some disadvantages. These disadvantages may include toxicity to aquatic life, corrosion of equipment during handling/storing/usage, oxidation of some types of organic matter creating more hazardous compounds, required higher doses in presence of chlorine-demanding materials, possible long-term effects of chlorine discharge into the environment, and the like.

Peracetic acid (PAA) may become a disinfectant of choice for water, medical, and food industries. PAA may be comparable to chlorine products with respect the effectiveness to kill pathogens. Additionally, conversion from a chlorine system to a PAA system may not require a complete retooling of existing facilities. PAA may be a stronger oxidant as compared to hypochlorite or chlorine dioxide. As with any disinfection agent, the concentration of the disinfection agent may be tailored to suit the needs of the facility. What is needed is a way to accurately measure PAA in an aqueous sample. Proper concentration of PAA in an aqueous sample may allow a facility to properly disinfect water, equipment, food, or the like.

Accordingly, an embodiment provides a technique for measuring peracetic acid in an aqueous sample through synthesis of a chromophore that can be used to detect aqueous peracetic acid (PAA) in the sample. In an embodiment, 4-(methylthio)aniline and at least one reactive species may be combined in a reactive solution to produce a chromophore/azo dye that has a measurable color. In an embodiment, the reactive species may include a chromotropic disodium salt, sodium nitrite, sodium 2-naphthol-6-sulfonate hydrate, 4-(methylthio)aniline, an aromatic thiomethyl ether group that is reactive to peracetic acid, any combination thereof, or the like. The chromophore may react with PAA in an aqueous solution, thereby causing a change to the chromophore that is detectable by way of the absorption profile. In an embodiment, the PAA may oxidize the methyl thioether substituent of the chromophore, thereby causing a colorimetric change in the chromophore. In an embodiment, a colorimetric change may be based upon a change in absorption, where the colorimetric change and/or change in absorption is proportional to the concentration of peracetic acid in the aqueous solution. Therefore, the amount of change of the color can be measured and correlated to the concentration of peracetic acid in the aqueous solution.

An embodiment comprises a chromophore which provides a color to the sample and may be detectable in the visible spectrum. An embodiment may use any suitable wavelength in the visible (such as red, yellow, or green), ultraviolet (UV), or infrared spectrums using techniques known in chemistry. In an embodiment, a chromophore reacts with PAA in an aqueous environment to produce a change in color easily detectable by photometric or other colorimetric measurement techniques. The absorbance at a desired measurement wavelength changes with respect to changing PAA concentrations over a certain range. The samples can be prepared such that any background absorbance from the reagents may be subtracted from the final measurement. Thus, a blank sample vial may be used in addition to the peracetic acid containing sample vial so that the colorimetric change of the peracetic acid containing sample vial may be compared to the blank sample vial.

Figure 1:
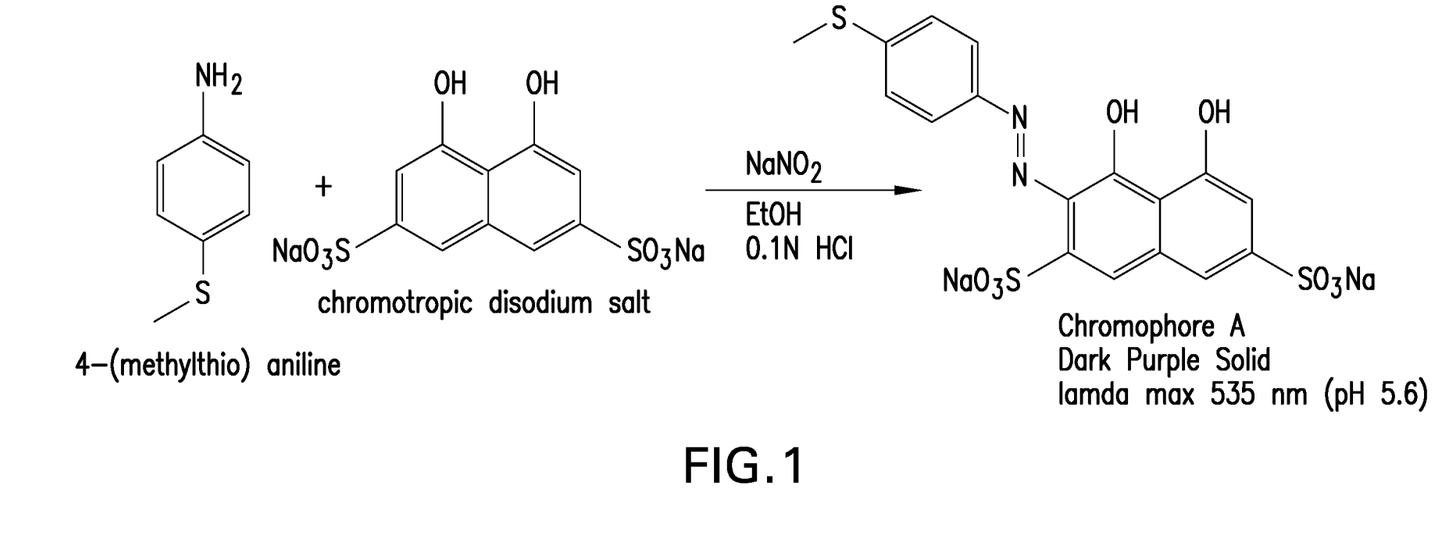
FIG. 1 illustrates a synthesis scheme of an embodiment.

Referring now to FIG. 1, a synthesis scheme of a chromophore of an embodiment is illustrated. In an embodiment, 4-(methylthio)aniline is combined with a reactive species in a solution. In an embodiment, the reactive species may be chromotropic acid disodium salt. The reactive solution may contain sodium nitrite, ethanol, hydrochloric acid, or the like. The hydrochloric acid may be 0.1N. In an embodiment, the synthesis scheme may produce a chromophore that is extremely sensitive to peracetic acid due to its high extinction coefficient. Thus, this chromophore may be useful for tests where the peracetic acid concentration may be between 0 and 25 ppm. This chromophore may be a dark purple solid. The chromophore may have a lambda max of 535 nanometers (nm) at pH 5.6.

Figure 2:
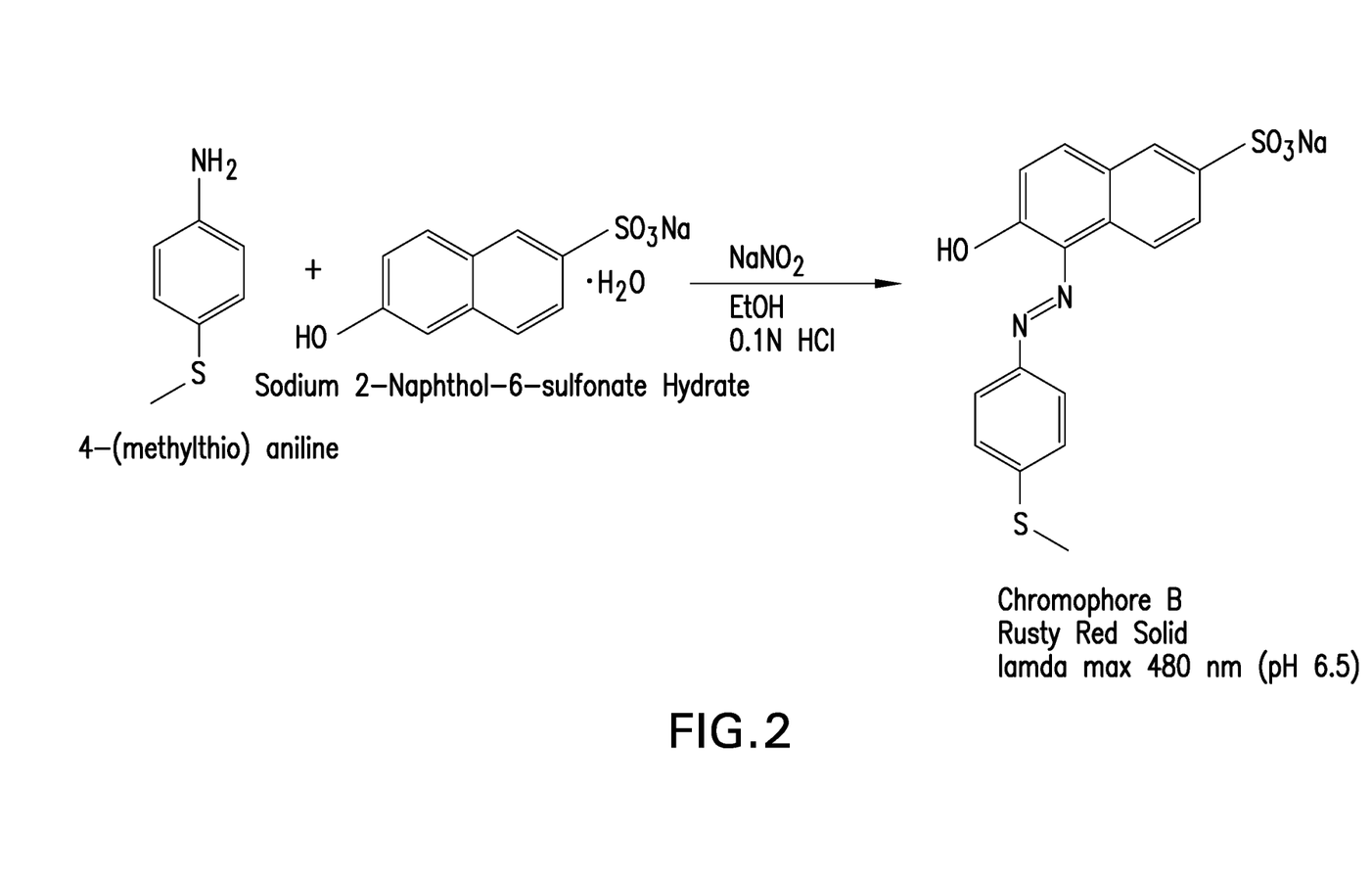
FIG. 2 illustrates a synthesis scheme of an embodiment.

Referring now to FIG. 2, another synthesis scheme of a chromophore of an embodiment is illustrated. In an embodiment, 4-(methylthio)aniline is combined with a reactive species in a reactive solution. In an embodiment, the reactive species may be sodium 2-naphthol-6-sulfonate hydrate. In an embodiment, the reactive solution may contain sodium nitrite, ethanol, hydrochloric acid, or the like. The hydrochloric acid may be 0.1N. In an embodiment, the synthesis scheme may produce a chromophore that is less sensitive than the previously mentioned chromophore due to its lower extinction coefficient. Thus, this chromophore may be useful for tests where the peracetic acid concentration may be between 40 and 500 ppm. This chromophore may be a rusty red solid. The chromophore may have a lambda max of 480 nm at pH 6.5.

Figure 3:
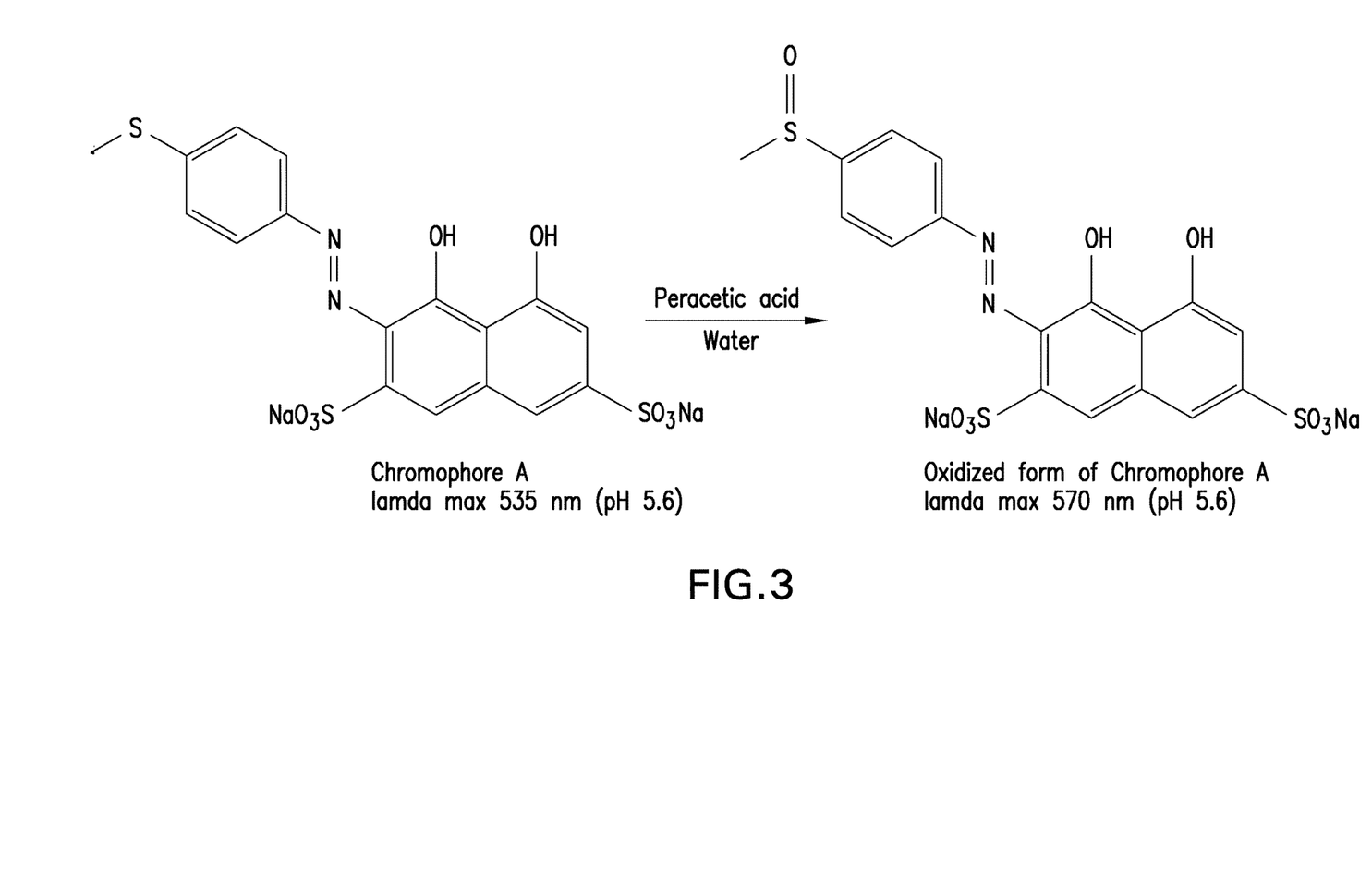
FIG. 3 illustrates a test scheme of an embodiment.

Referring now to FIG. 3, an embodiment test scheme of a chromophore is illustrated. For example, the chromophore produced in FIG. 1 may be used. The chromophore may be sensitive to peracetic acid in an aqueous solution. For example, the chromophore from FIG. 1 may have a lambda max of 535 nm at a pH of 5.6. When the chromophore is placed in an aqueous solution containing peracetic acid, the chromophore may be oxidized. The oxidation of the chromophore may shift the lambda max to a new value, thereby causing a change in the color of the chromophore, and thus, a change in color of the aqueous solution. For example, the lambda max of the chromophore may shift from 535 nm to 570 nm at a pH of 5.6. Values are for example purposes and other values of lambda max may be observed by different chromophores and/or at different pH values.

Figure 4:
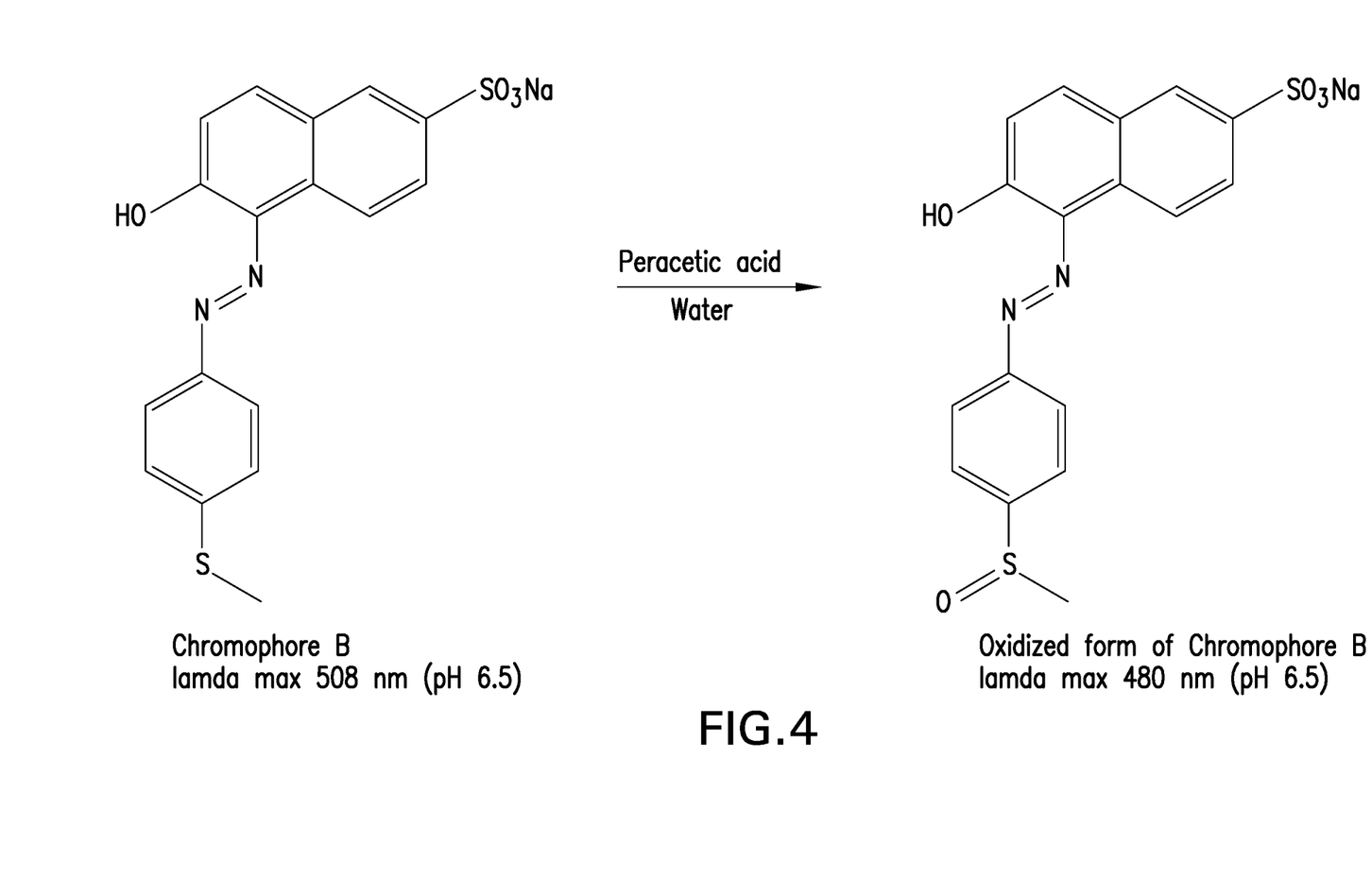
FIG. 4 illustrates a test scheme of an embodiment.

Referring now to FIG. 4, another embodiment test scheme of a chromophore is illustrated. For example, the chromophore produced in FIG. 2 may be used. The chromophore may be sensitive to peracetic acid in an aqueous solution. For example, the chromophore from FIG. 2 may have a lambda max of 508 nm at a pH of 6.5. If the chromophore is placed in an aqueous solution containing peracetic acid, the chromophore may be oxidized. The oxidation of the chromophore may shift the lambda max to a new value, thereby causing a change in the color of the chromophore, and thus, a change in color of the aqueous solution. For example, the lambda max of the chromophore may shift from 508 nm to 480 nm at a pH of 6.5. Values are for example purposes and other values of lambda max may be observed by different chromophores and/or at different pH values.

Figure 5A:
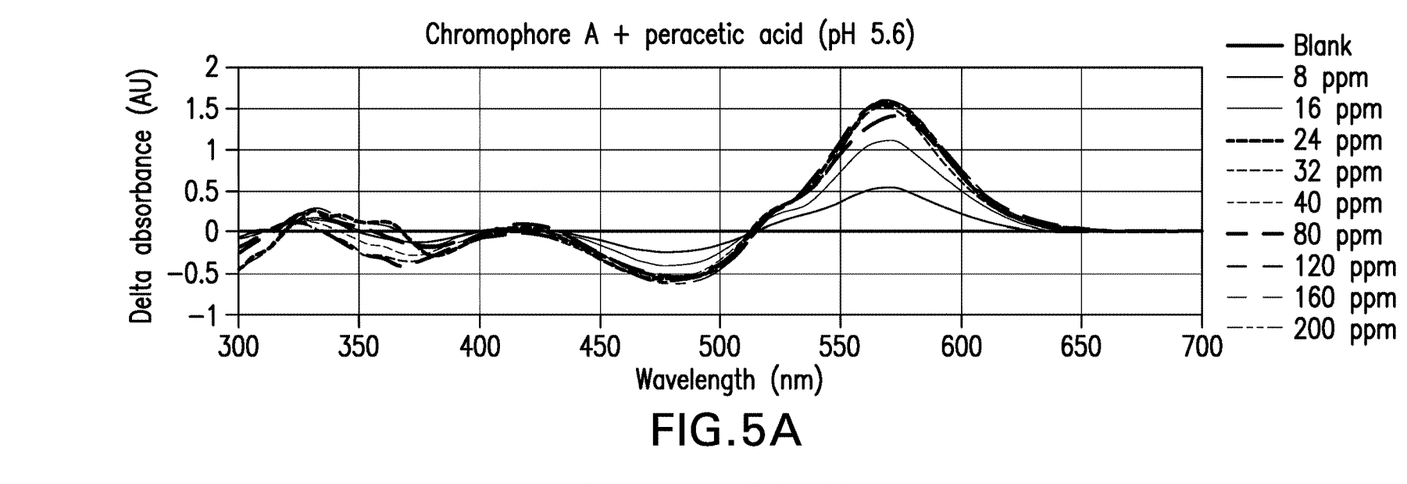
FIG. 5A and FIG. 5B illustrate a wavelength scan and response curve of an embodiment.
Figure 5B:
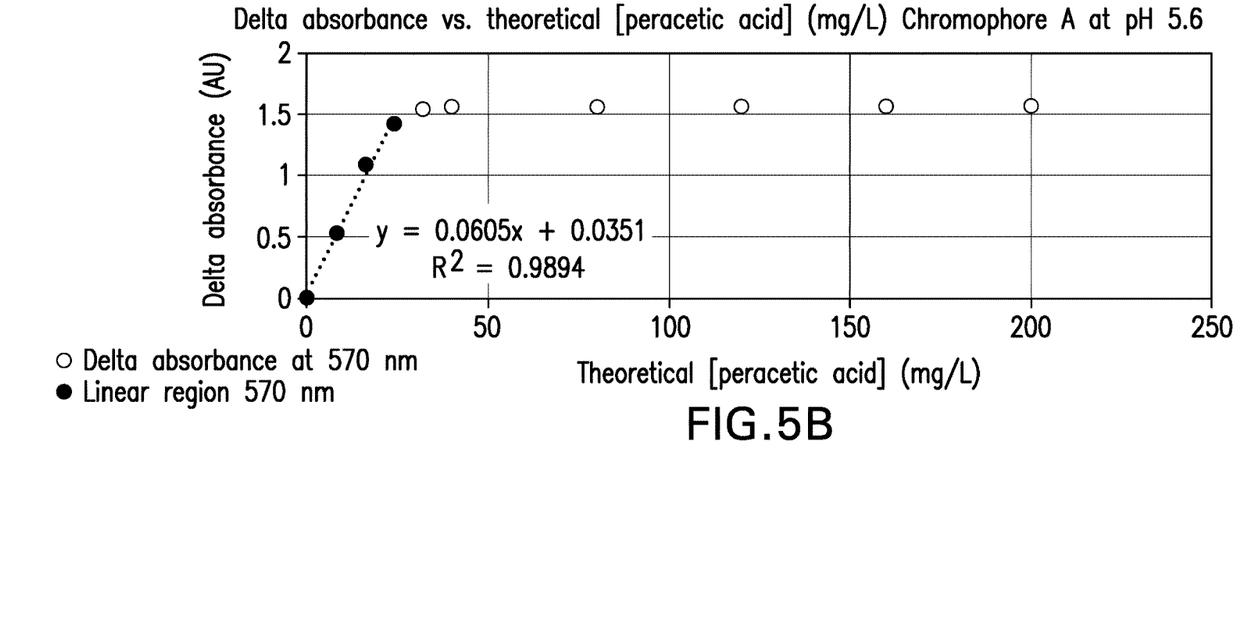

Referring now to FIG. 5, an example wavelength scan and response curve is illustrated for the chromophore of FIG. 1 and FIG. 3. In the illustrated examples of FIG. 5, the aqueous solution containing the peracetic acid and the chromophore is pH 5.6. In FIG. 5A, a delta absorbance (measured in absorbance units (AU)) is plotted against a wavelength (measured in nanometers (nm)). The plot also shows different curves for different concentrations of peracetic acid ranging from a blank (zero concentration) to 200 parts per million (ppm) as gray scale plots. The chromophore may display a peak delta absorbance around 570 nm. The chromophore also shows an increase in delta absorbance with increasing concentrations of peracetic acid present in the aqueous solution. In FIG. 5B, delta absorbance (AU) is plotted against theoretical peracetic acid concentration (mg/L). The chromophore may have a linear region of about 0-25 mg/L PAA when measured at 570 nm at a pH of 5.6.

Figure 6A:
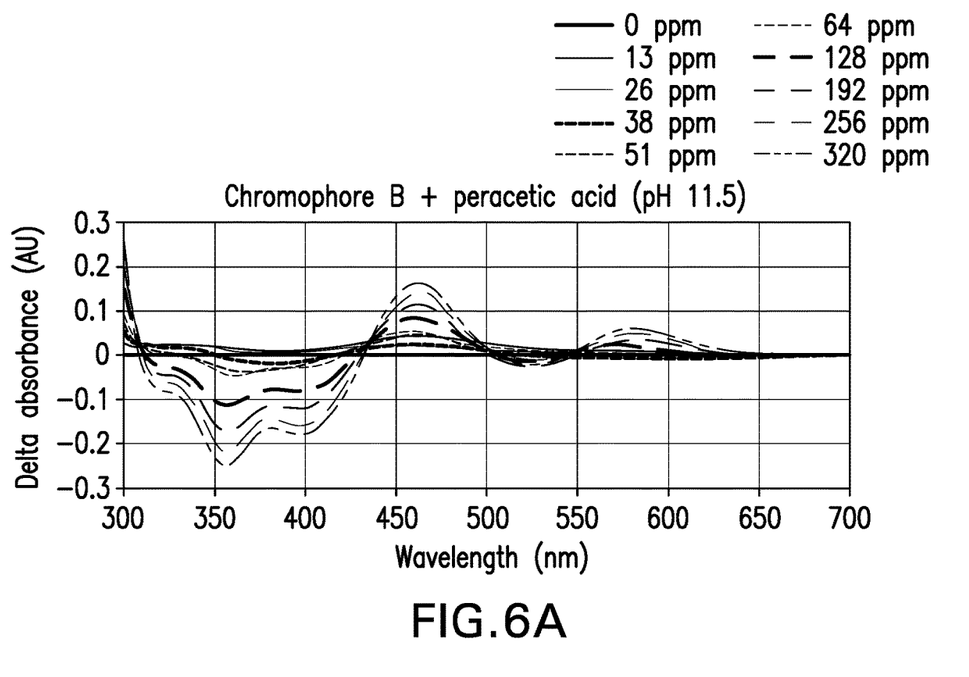
FIG. 6A and FIG. 6B illustrate a wavelength scan and response curve of an embodiment.
Figure 6B:
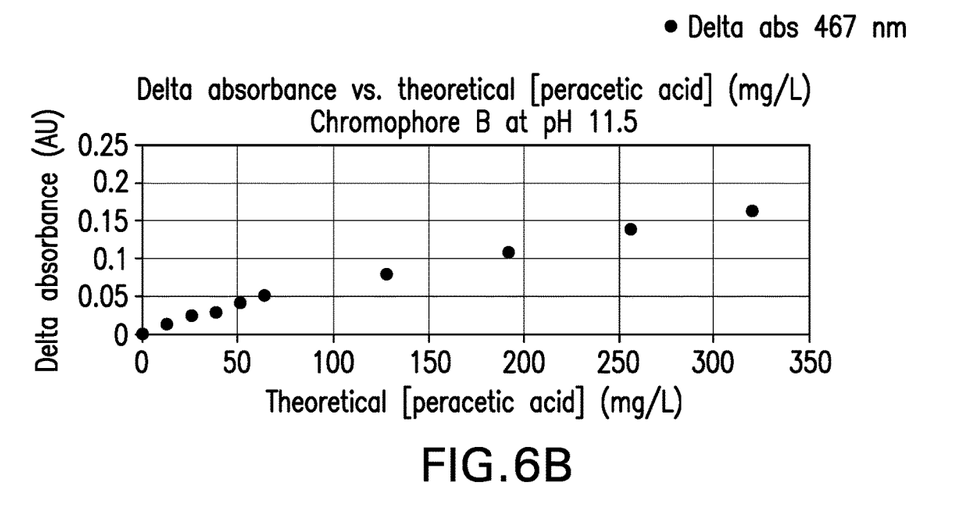

Referring now to FIG. 6, another example of a wavelength scan and dose response curve is illustrated for the chromophore of FIG. 2 and FIG. 4. In the illustrated examples of FIG. 6, the aqueous solution containing the peracetic acid and the chromophore is pH 11.5. In FIG. 6A, a delta absorbance (measured in absorbance units (AU)) is plotted against a wavelength (measured in nanometers (nm)). The plot also shows different curves for different concentrations of peracetic acid ranging from a blank (zero concentration) to 320 (ppm) as gray scale plots. The chromophore may display a peak delta absorbance around 467 nm. The chromophore also shows an increase in delta absorbance with increasing concentrations of peracetic acid present in the aqueous solution. In FIG. 6B, delta absorbance (AU) is plotted against theoretical peracetic acid concentration (mg/L). The chromophore may have a linear region from 0-325 mg/L peracetic acid when measured at 467 nm at a pH of 11.5.

Figure 7A:
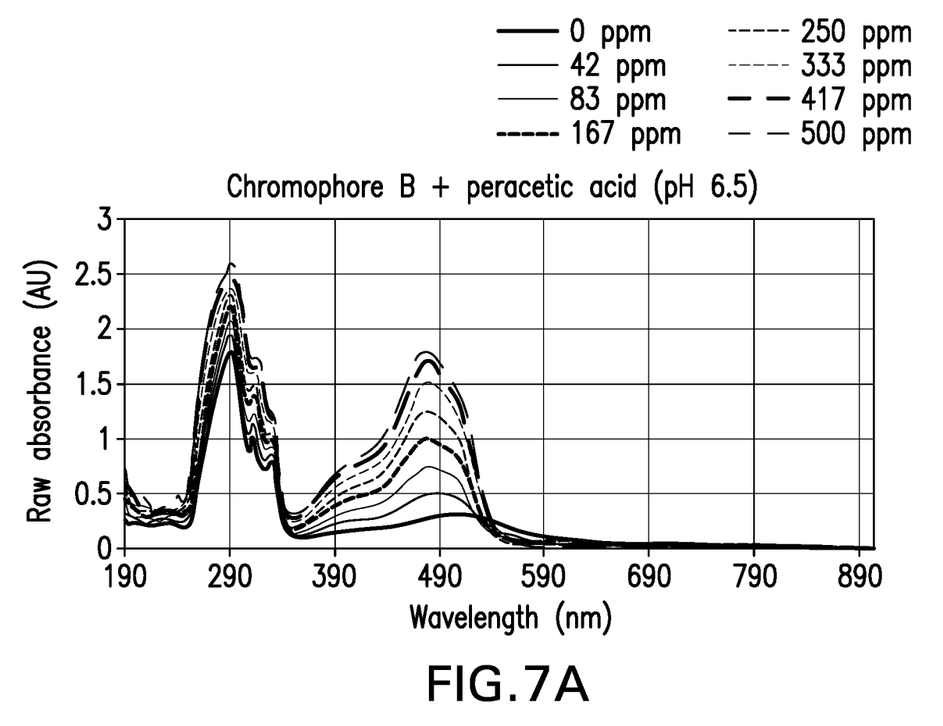
FIG. 7A and FIG. 7B illustrate a wavelength scan and response curve of an embodiment.
Figure 7B:
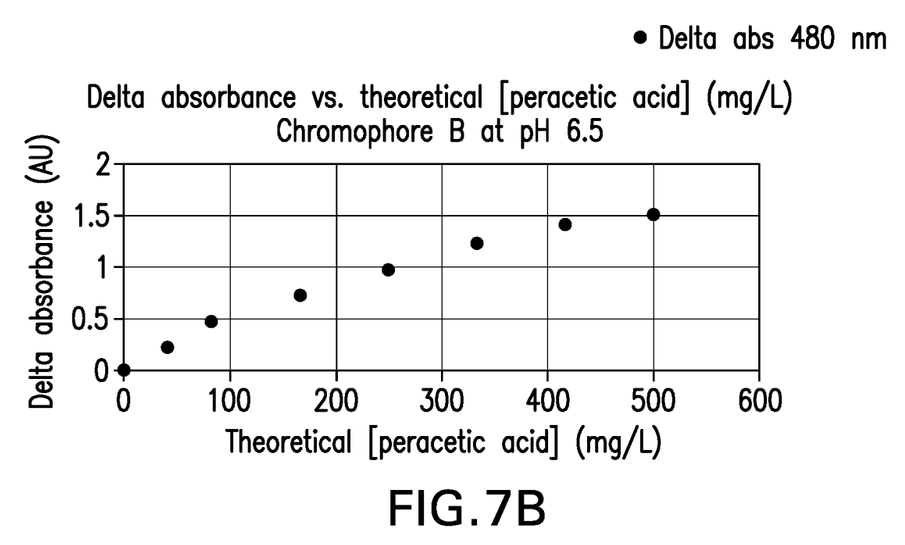

Referring now to FIG. 7, a further example of a wavelength scan and dose response curve is illustrated for the chromophore of FIG. 2 and FIG. 4. In the illustrated examples of FIG. 7, the aqueous solution containing the peracetic acid and the chromophore is pH 6.5. In FIG. 7A, a raw absorbance (measured in absorbance units (AU)) is plotted against a wavelength (measured in nanometers (nm)). The plot also shows different curves for different concentrations of peracetic acid ranging from a blank (zero concentration) to 500 (ppm) as gray scale plots. The chromophore may display two peaks of absorbance around 290 nm and 480 nm. The chromophore also shows an increase in raw absorbance with increasing concentrations of peracetic acid present in the aqueous solution. In FIG. 7B, delta absorbance (AU) is plotted against theoretical peracetic acid concentration (mg/L). The chromophore may have a linear region from 0-500 mg/L peracetic acid when measured at 480 nm at a pH of 6.5.

In an embodiment the presence of peracetic acid in an aqueous solution may cause a shift in the absorption of a chromophore. Examples of this shift in absorbance may be illustrated in FIG. 5, FIG. 6, and FIG. 7. Therefore, the absorbance at a specified wavelength, of an aqueous sample containing peracetic acid may be correlated to the concentration of peracetic acid in the aqueous solution. In other words, the oxidation of the chromophore caused by the peracetic acid in the aqueous solution causes a change in absorbance at a given wavelength for the chromophore and/or aqueous solution. This change in absorbance is measurable and able to be correlated to the concentration of peracetic acid within the aqueous solution. Absorption curves may be generated for a range of peracetic acid concentrations. Absorption curves may be generated for a range of pH values of the aqueous solution. Absorption curves may be generated for different chromophores. Absorption curves may be generated for any different condition that may affect absorption values such as temperature, sample content, turbidity, viscosity, measurement apparatus, aqueous sample chamber, or the like.

The change in absorption may be measured using a spectrophotometer. Spectrophotometry is measurement of reflection or transmission properties of a sample measure as a wavelength. Spectrophotometry may be a quantitative measure of how much light is absorbed by a material. This material may be a chromophore sensitive to peracetic acid in an aqueous sample. The change in absorption may also be measured using other colorimetric measurement devices.

To determine the amount of peracetic acid in the sample, the resulting measurement can be determined based upon a calibration curve. The calibration curve is built based on the chromophore species for a predetermined range. The absorbance of the sample can be used to determine the concentration of peracetic acid in solution. In other words, a higher peracetic acid concentration results in a greater absorbance, or vice versa depending on the curve. Calibration may be verified periodically to ensure proper compliance with standards or regulatory agency requirements.

A colorimetric cell may contain an aqueous sample, a chromophore, and associated reagents. An analyzer may contain one or more bottles of reagents which contain necessary reagents such as, but not limited to, the chromophore, buffers, or any reagent that may not be premixed before the sampling process. The regents contained in the one or more bottles may be pump fed or gravity fed. The flow of the reagents may be metered to ensure proper volume delivery to the colorimetric cell. The aqueous sample may be fed through a pressured inlet, a vessel, or the like. The aqueous sample may be introduced into the colorimetric chamber by a pump or gravity fed. The sampling device may be in series or parallel to an aqueous flow. The device may have a system to ensure proper mixing of the aqueous sample, a chromophore, and related reagents.

The peracetic acid concentration may be an output upon a device in the form of a display, printing, storage, audio, haptic feedback, or the like. Alternatively or additionally, the output may be sent to another device through wired, wireless, fiber optic. Bluetooth®, near field communication, or the like. An embodiment may use an alarm to warn of peracetic acid concentration outside acceptable levels. An embodiment may use a system to shut down water output or shunt water from sources with unacceptable levels of peracetic acid. For example, a peracetic acid measuring device may use a relay coupled to an electrically actuated valve, or the like.

A chromophore species and related reagents may be added to a known volume of an aqueous sample. The resulting color changing mixture may then be placed in a device to measure the absorbance, for example a spectrophotometer. Alternatively, the resulting color change of the aqueous sample may be compared to a card of color bands to determine peracetic acid concentration correlated to the color change from the presence of peracetic acid.

An embodiment may use a test strip. The test strip may contain the chromophore species and related reagents. The test strip may be dipped into the sample solution, or a known volume of sample solution may be placed on the test strip. The test strip may then be placed in a device to measure the color change.

The chromophore for the detection of aqueous peracetic acid may have an advantage over current techniques. The chromophores described herein may be able to detect peracetic acid at low ranges. Additionally, the test does not use DPD. DPD may be used in traditional techniques to produce color quantitatively in a sample. However, DPD may have drawbacks with both stability and interferences within a sample. The described chromophore technique may also be used at high ranges (i.e. 500 ppm) of peracetic acid concentrations without the need to dilute a sample. Traditional DPD tests may only have a range to about 10 ppm and associated stability issues. Also, replacing peracetic acid in lieu of chlorine for disinfection has benefits such as safer handling, safer storage, less corrosive to equipment, and removal of chlorine from effluent with may have environmental impact on waterways and organisms outside the areas of treatment. Thus, the techniques as described herein provide an environmentally safe or "green" benefit.

This disclosure has been presented for purposes of illustration and description but is not intended to be exhaustive or limiting. Many modifications and variations will be apparent to those of ordinary skill in the art. The embodiments were chosen and described in order to explain principles and practical application, and to enable others of ordinary skill in the art to understand the disclosure for various embodiments with various modifications as are suited to the particular use contemplated.

Thus, although illustrative example embodiments have been described herein with reference to the accompanying figures, it is to be understood that this description is not limiting and that various other changes and modifications may be affected therein by one skilled in the art without departing from the scope or spirit of the disclosure.

What is claimed is:

1. A method for measuring peracetic acid concentration in an aqueous solution, comprising:
   combining, in a reactive solution, 4-(methylthio)aniline and at least one reactive species to produce a chromophore, wherein the at least one reactive species comprises a chromotropic acid disodium salt;
   placing the chromophore in an aqueous solution, wherein the aqueous solution comprises peracetic acid, wherein peracetic acid within the aqueous solution reacts with the chromophore; and
   measuring a concentration of peracetic acid within the aqueous solution, wherein the measuring comprises quantifying a colorimetric change of the aqueous solution caused by the peracetic acid reacting with the chromophore.

2. The method of claim 1, wherein the reactive solution comprises sodium nitrite.

3. The method of claim 1, wherein the reactive solution comprises ethanol.

4. The method of claim 1, wherein the reactive solution comprises hydrochloric acid.

5. The method of claim 1, wherein the peracetic acid reacts with the chromophore by oxidizing the chromophore.

6. The method of claim 1, wherein the chromophore comprises an aromatic thiomethyl ether group that is reactive to peracetic acid.

7. The method of claim 1, wherein the chromophore is sensitive to peracetic acid in an amount between 0-25 parts per million in the aqueous solution.

8. A method for measuring peracetic acid concentration in an aqueous solution, comprising:
   combining, in a reactive solution, 4-(methylthio)aniline and at least one reactive species to produce a chromophore, wherein the at least one reactive species comprises sodium 2-naphthol-6-sulfonate hydrate;
   placing the chromophore in an aqueous solution, wherein the aqueous solution comprises peracetic acid, wherein peracetic acid within the aqueous solution reacts with the chromophore; and
   measuring a concentration of peracetic acid, wherein the measuring comprises quantifying a colorimetric change of the aqueous solution caused by the peracetic acid reacting with the chromophore.

9. The method of claim 8, wherein the reactive solution comprises sodium nitrite.

10. The method of claim 8, wherein the reactive solution comprises ethanol.

11. The method of claim 8, wherein the reactive solution comprises hydrochloric acid.

12. The method of claim 8, wherein the chromophore comprises an aromatic thiomethyl ether group that is reactive to peracetic acid.

* * * * *